US00PP17205P3

(12) United States Plant Patent
Jensen et al.

(10) Patent No.: US PP17,205 P3
(45) Date of Patent: Nov. 14, 2006

(54) *CAMPANULA* PLANT NAMED 'PKMP01'

(50) Latin Name: *Campanula portenschlagiana*
Varietal Denomination: PKMp01

(75) Inventors: Gert Kim Jensen, Odense (DK); Per Elmegaard Andersen, Skalskor (DK)

(73) Assignees: Gartneriet PKM APS, Odense (DK); Gartneriet Elmegaard Andersen, Skalskor (DK)

( * ) Notice: Subject to any disclaimer, the term of this patent is extended or adjusted under 35 U.S.C. 154(b) by 268 days.

(21) Appl. No.: 10/648,304

(22) Filed: Aug. 27, 2003

(65) Prior Publication Data

US 2004/0244084 P1 Dec. 2, 2004

(30) Foreign Application Priority Data

May 26, 2003 (QZ) ..... 2003/0982

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP14,597 P2 * 3/2004 Jensen ..... Plt./263
PP14,897 P2 * 6/2004 Jensen ..... Plt./263

FOREIGN PATENT DOCUMENTS

EP 1230841 A1 * 8/2002
EP 1230842 A1 * 8/2002

OTHER PUBLICATIONS

UPOV ROM GTITM Computer Database, GTI Jouve Retrieval Software 2004/04 Citation(s) for '08.01.17' and 'PKMp01'.*
http://www.inspection.gc.ca/plaveg/pbrpov/cropreport/cam/app00004558e.shtml.*

* cited by examiner

*Primary Examiner*—Kent Bell
*Assistant Examiner*—W. C. Haas
(74) *Attorney, Agent, or Firm*—Foley & Lardner, LLP

(57) ABSTRACT

A distinct cultivar of *Campanula* plant named 'PKMp01', characterized by having compact, upright plant habit; dense and bushy plant form mainly due to more upright stems; vigorous growth habit and less need for chemical growth retardation; greater number of flowers per plant; large upright blue flowers, and no need for vernalization.

4 Drawing Sheets

Latin name of the genus and species of the plant claimed: *Campanula portenschlagiana.*
Variety denomination: 'PKMp01'.

BACKGROUND OF THE INVENTION

The present Invention relates to a new and distinct cultivar of *Campanula* plant, botanically known as *Campanula portenschlagiana Schult*., commonly known as Dalmatian Bellflower, and hereinafter referred to by the name 'PKMp01'.

The new *Campanula* is a product of a planned breeding program conducted by the Inventors, Gert K. Jensen and Per Elmegaard Andersen, in Søhus, Denmark. The new *Campanula* originated from a cross made in 2001 by the Inventors between a proprietary selection of *Campanula portenschlagiana Schult* named '08.08' (unpatented) as the female parent, and a proprietary selection of *Campanula portenschlagiana Schult* named '08.98.05' (unpatented) as the male parent. The Inventors selected the new *Campanula* cultivar from the progeny of the above crossing in 2001 on the basis of its compact and freely flowering habit. Plants of the new *Campanula* are more upright, compact and more freely flowering than plants of both parental selections.

Asexual reproduction of the new cultivar by terminal cuttings taken and propagated in Søhus, Denmark, has shown that the unique features of this new *Campanula* are stable and reproduce true to type in many successive generations.

SUMMARY OF THE INVENTION

Plants of the cultivar 'PKMp01' have not been observed under all possible environmental conditions. The phenotype may vary somewhat with variations in environment such as temperature, light intensity, day length, and fertility level without, however, any variance in genotype.

The following traits have been repeatedly observed and are determined to be the unique characteristics of 'PKMp01'. These characteristics in combination distinguish 'PKMp01' as a new and distinct cultivar:

1. Compact, upright plant habit;
2. Dense and bushy plant form, mainly due to more upright stems;
3. Vigorous growth habit, less need for chemical growth retardation;
4. Greater number of large flowers per plant;
5. Large upright blue flowers; and
6. No need for vernalization.

Side-by-side comparisons between the instant plant and the parental cultivars, '08.08' and '08.98.05', were conducted by the Inventors in Stige, Denmark. Plants of 'PKMp01' differ from the cultivars '08.08' and '08.98.05' in the following characteristics:

1. Plants of 'PKMp01' have shorter internodes and shorter leaves than plants of the cultivars '08.08' and '08.98.05'.

2. Plants of 'PKMp01' have light gray-green colored leaves whereas plants of the cultivars '08.08' and '08.98.05' have green-colored leaves.
3. Plants of 'PKMp01' have shorter flower peduncles than plants of the cultivars '08.08' and '08.98.05'.
4. Plants of 'PKMp01' are shorter and more compact than plants of the cultivars '08.08' and '08.98.05'.
5. Plants of 'PKMp01' have more flowers per plant and larger flowers than plants of the cultivars '08.08' and '08.98.05'.

BRIEF DESCRIPTION OF THE PHOTOGRAPHS

The accompanying photographic drawings illustrate the overall appearance of the new cultivar, showing the colors as true as it is reasonably possible to obtain in colored reproductions of this type. Colors in the photographs may differ slightly from the color values cited in the detailed botanical description, which accurately describe the colors of 'PKMp01'.

The first photographic drawing shows a side perspective view of a typical flowering plant of 'PKMp01', designated in the photograph by the breeder's reference '08.01.17'. The second photographic drawing shows a top perspective view of a typical flowering plant of 'PKMp01', designated in the photograph by the breeder's reference '08.01.17'. The third photographic drawing shows on the left, a flower of the male parental cultivar '08.98.05', which is compared on the right to a flower of the new *Campanula* cultivar, 'PKMp01', designated in the photograph by the breeder's reference '08.01.17'.

The fourth photographic drawing shows on the left, a flower of the female parental cultivar '08.08', which is compared on the right to a flower of the new *Campanula* cultivar, 'PKMp01', designated in the photograph by the breeder's reference '08.01.17'.

DETAILED BOTANICAL DESCRIPTION

In the following description, color references are made to The Royal Horticultural Society (R.H.S.) Colour Chart 4$^{th}$ edition.

The aforementioned photographs, together with the following observations, measurements and values describe plants of the new *Campanula* cultivar 'PKMp01' as grown in a heated and lighted greenhouse in Søhus, Denmark, under conditions which closely approximate those generally used in commercial practice. The plants were grown in an average day temperature of 18–22° C. and an average night temperature 16° C. The light level the plants were grown in is 55 W per m$^2$. The age of the plants described is about 13–14 weeks old after cutting, as grown in 11 cm pots.

Botanical classification: *Campanula portenschlagiana Schult.*

Parentage:

*Female parent.*—*Campanula portenschlagiana Schult.* '08.08'.

*Male parent.*—*Campanula portenschlagiana Schult.* '08.98.05'.

Propagation: Terminal vegetative cuttings.

Time to initiate roots: About 10 to 14 days at 18 to 21° C. in tunnels in a greenhouse.

Root description: Fine, well branched; color: RHS 159D.

Plant description:

*Form.*—Perennial, herbaceous plant with upright plant habit, and overall globular shape with upright stems. Campanulate flowers in racemes. Freely branching with lateral branches forming at every node; dense and bushy.

*Crop time.*—After rooting, about 14 weeks are required to produce finished flowering plants in 11 cm pots.

*Plant height* (*soil level to top of plant plane*).—About 13 cm.

*Plant spread.*—23–27 cm.

*Lateral branches.*—Average number 65–75, average length 11–13 cm, average branch diameter 1–2 mm, 5–7 leaves per lateral branch.

*Internode length.*—15 mm.

*Stem.*—RHS 143B in color.

*Vigor.*—Vigorous growth rate.

*Foliage description.*—Leaves single, palmate venation. Length: 15–20 mm. Width: About 25 mm. Shape: cordate. Apex: broad acuminate. Base: cordate. Margin: broadly dentate. Texture: smooth, glabrous, dull. Short stiff hairs on abaxial side and along veins and margin. Color: Young foliage, upper and lower surfaces: 137A, green. Mature foliage, upper surface: N139C, lower surface 139B. Venation, 138D, palmate venation pattern.

Petiole.—4–6 cm in length, 1–2 mm diameter, smooth, glabrous texture, RHS N138D in color.

Flower description:

*Flower arrangement and shape.*—Single, upright flowers in racemes; campanulate flowers with small star shaped calyx.

*Natural flowering season.*—Continuous throughout the spring and summer. Season can be extended by vernalization and long day treatments.

*Flower longevity on the plant.*—Average flower longevity is about 20–30 days. Longevity of individual flowers is highly dependent on temperature and light conditions. Flowers persistent.

*Number of flowers per inflorescence.*—4–5.

*Inflorescence size.*—Length: about 11 cm.

*Flowers.*—Depth: about 20 mm. Diameter: about 25 mm. Lanceolate petal lobes: 10 mm long and 7 mm wide. Corolla color: blue, upper surfaces N87B, lower surface N87C, white lines along fusion margins of petals.

*Buds.*—Length: up to 15 mm, diameter: up to 4 mm, oblong, ridged shape, color: white to N88B.

*Petals:*—Arrangement: single, sympetalous; overall shape; bell-shaped, campanulate; 5 in number, basally fused, entire margin, acute apex, length 8–10 mm, width: 7 mm, petal color: upper surfaces RHS N87B, lower surfaces color RHS N87C; velvety texture.

*Sepals.*—Shiny, glabrous, free arrangement, 5 in number, cuspidate apex, fused base, length: 3 mm, width: 1 mm, margin shape: linear with arrow-shaped tip, color: immature RHS 144B (both surfaces); mature RHS 138A (both surfaces).

*Penduncle.*—Strength: moderately strong. Length: about 25 mm. Diameter: about 1 mm. Color: 138D light green.

Reproductive organs:

*Stamen.*—5, fused until pollen is shed.

*Anther.*—1 mm in diameter size. Shape: fused, after shedding curling. Color RHS 158B.

*Pollen.*—RHS 158B, average production.

*Pistil.*—1, 12 mm in length, tripartite shape.

*Stigma.*—Conspicuous tripartite, color: 85A blue.

*Style.*—Length.—11 mm, color RHS 84B.

*Ovary.*—RHS 150D.

*Seed.*—Average number: about 20–30. Length: about 1 mm. Diameter: about 0.3 mm.

Disease pest resistance: None observed.

Disease susceptibility: None observed.

Weather tolerance: Plants of the new *Campanula* have exhibited good tolerance to draught, rain and wind, low temperature resistant to −15° C.

We claim:

1. A new and distinct cultivar of *Campanula* plant named 'PKMp01', as illustrated and described herein.

* * * * *

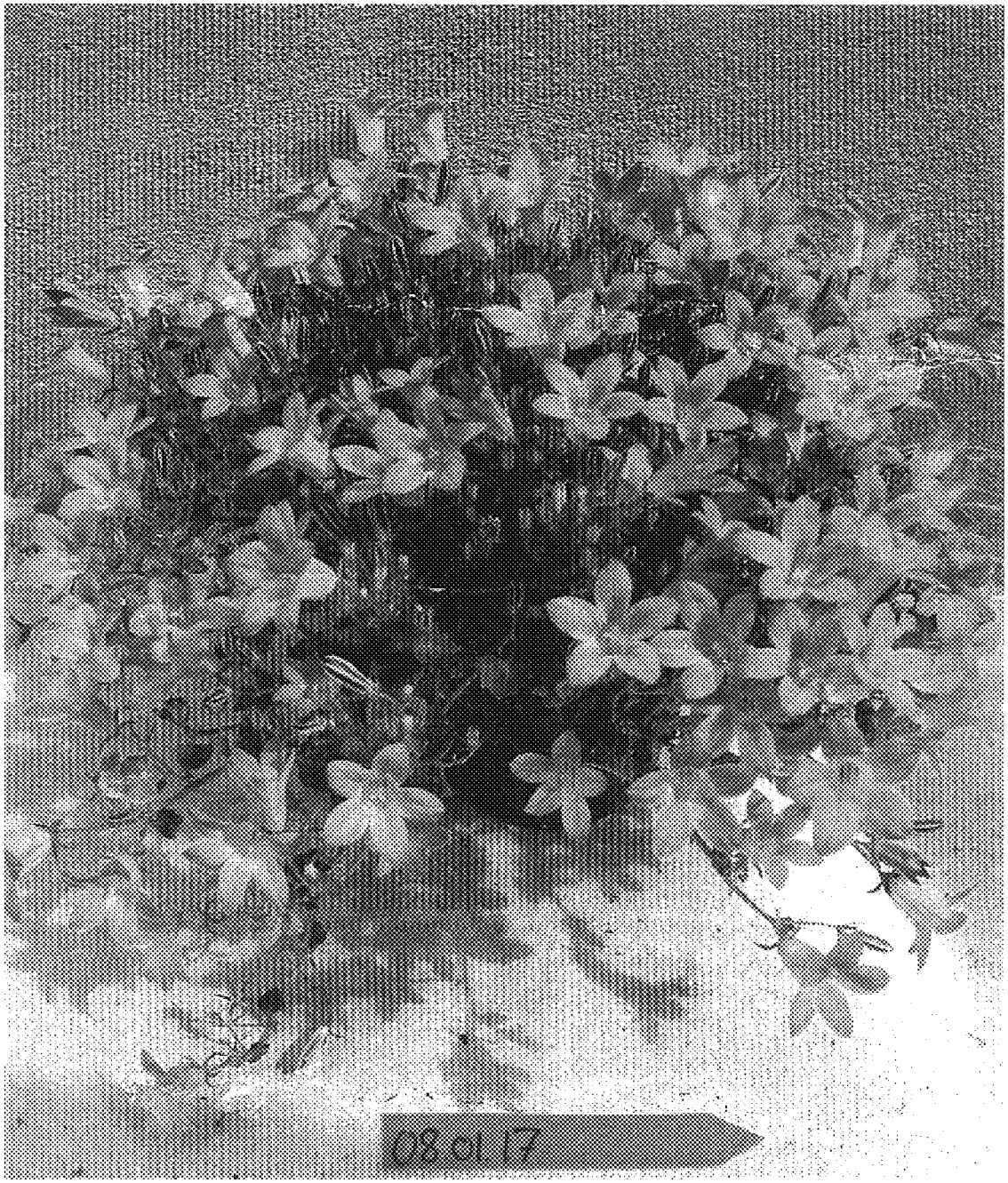
02 of 17

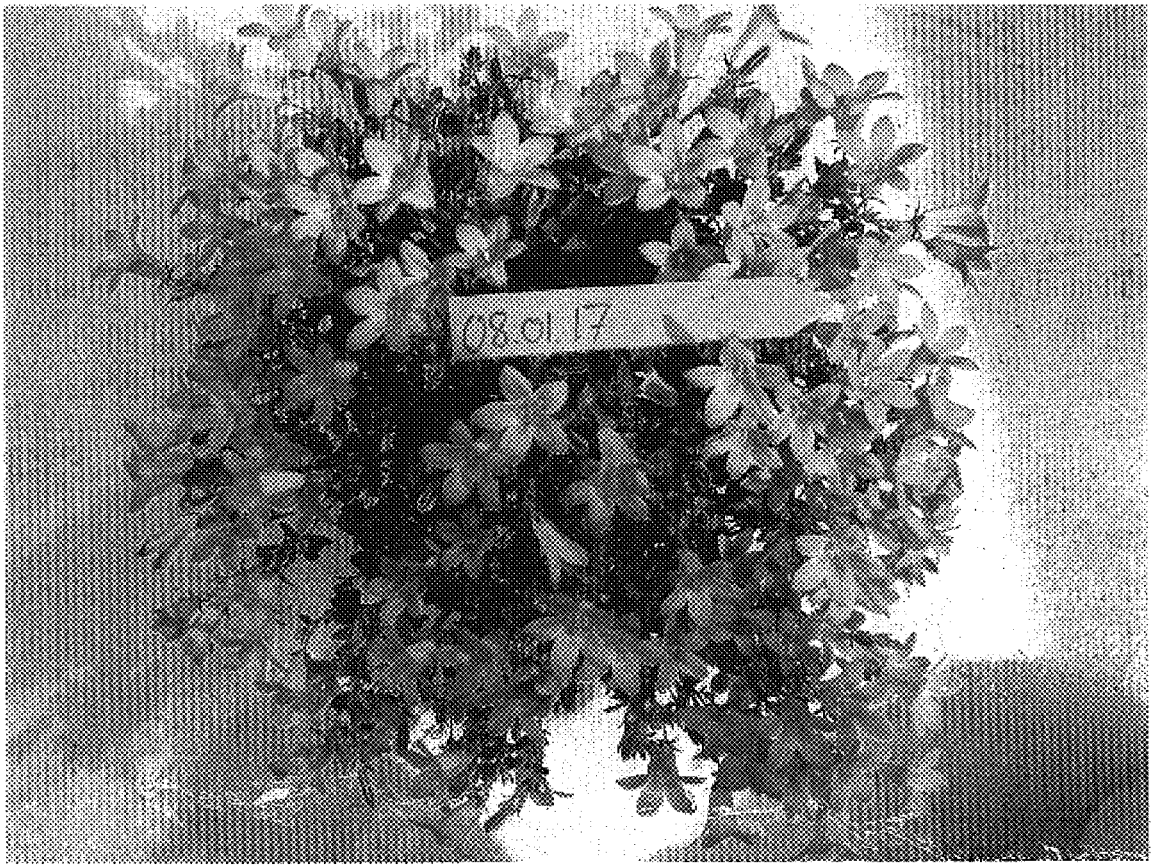
08 cl 17

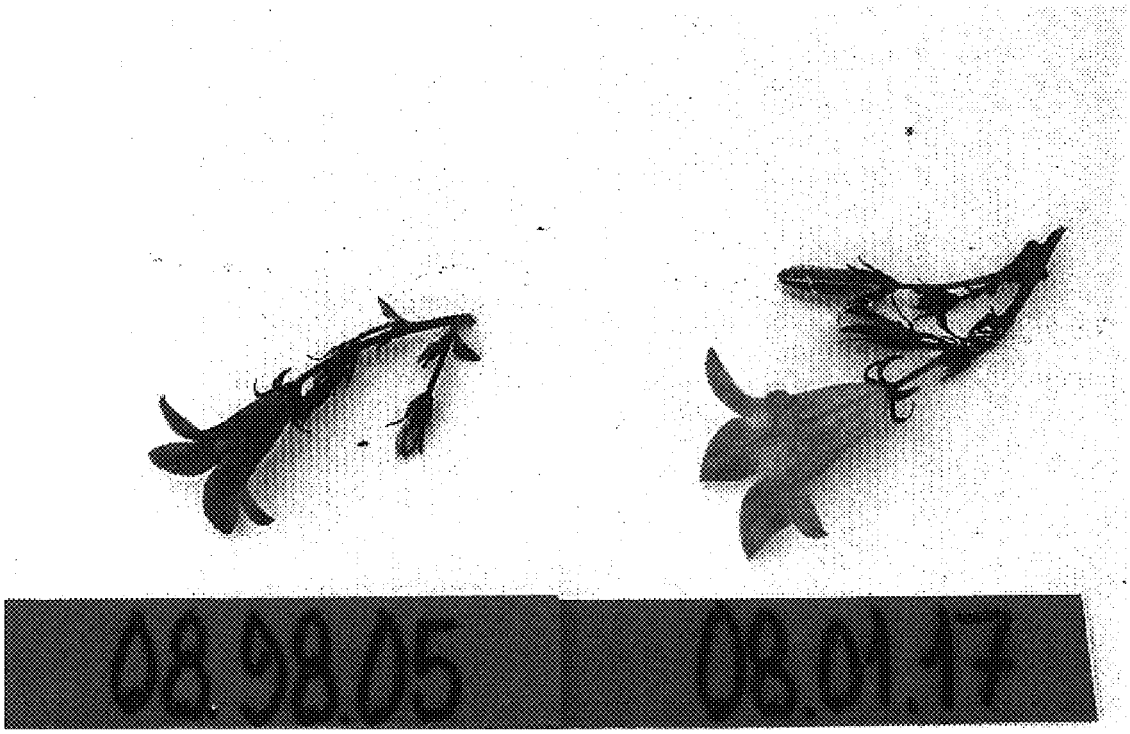
08 98 05
08 01 17

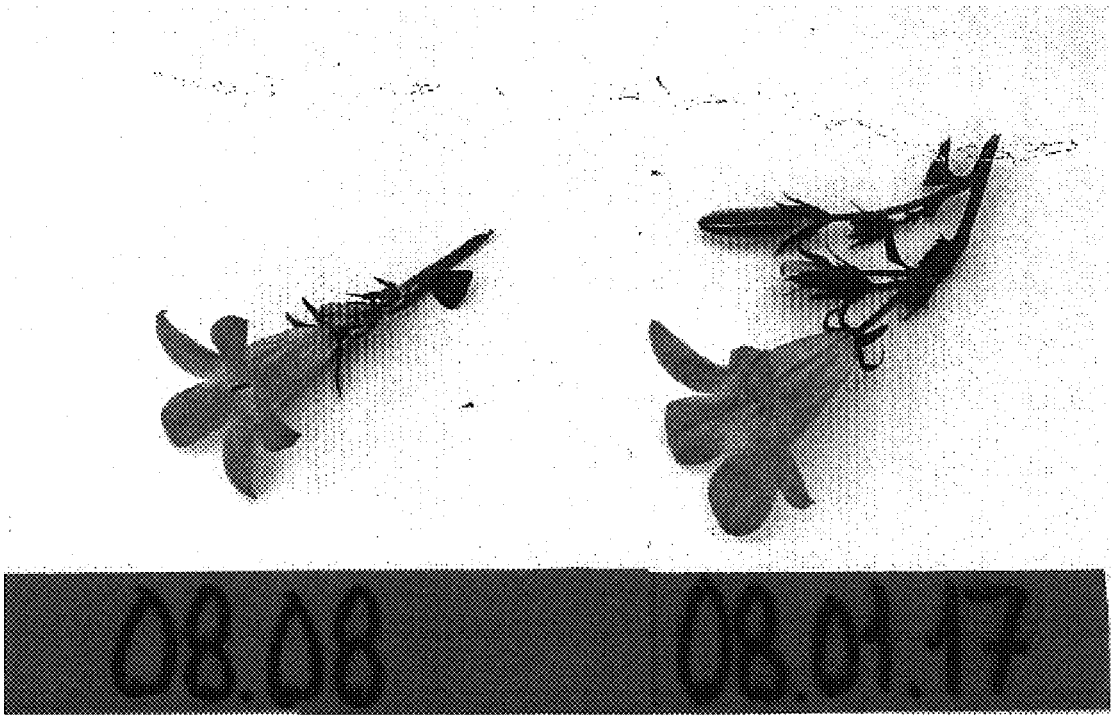
08.08
08.47